United States Patent
Lin et al.

(10) Patent No.: US 12,349,970 B2
(45) Date of Patent: Jul. 8, 2025

(54) GUIDING FIXATION METHOD APPLIED TO EYE EXAMINATION DEVICE

(71) Applicant: Crystalvue Medical Corporation, Taoyuan (TW)

(72) Inventors: Chun Nan Lin, Bade (TW); Kun Cheng Hsieh, New Taipei (TW)

(73) Assignee: Crystalvue Medical Corporation, Taoyuan (TW)

(*) Notice: Subject to any disclaimer, the term of this patent is extended or adjusted under 35 U.S.C. 154(b) by 491 days.

(21) Appl. No.: 17/901,426

(22) Filed: Sep. 1, 2022

(65) Prior Publication Data
US 2023/0074556 A1  Mar. 9, 2023

(30) Foreign Application Priority Data
Sep. 6, 2021 (TW) .................................. 110133091

(51) Int. Cl.
*A61B 3/00* (2006.01)
(52) U.S. Cl.
CPC .......... *A61B 3/0091* (2013.01); *A61B 3/0008* (2013.01); *A61B 2562/0257* (2013.01)
(58) Field of Classification Search
CPC ................ A61B 3/0091; A61B 3/0008; A61B 2562/0257
USPC ............................................... 351/221
See application file for complete search history.

(56) References Cited

U.S. PATENT DOCUMENTS

| | | | |
|---|---|---|---|
| 7,290,878 B1* | 11/2007 | Hofeldt | A61B 3/08 351/200 |
| 2004/0155834 A1* | 8/2004 | Wit | G09G 3/025 345/7 |
| 2013/0100400 A1* | 4/2013 | Hofeldt | A61B 3/022 351/201 |
| 2019/0099076 A1* | 4/2019 | Fujikado | A61B 3/10 |

\* cited by examiner

*Primary Examiner* — Sharrief I Broome
(74) *Attorney, Agent, or Firm* — Patterson + Sheridan, LLP

(57) ABSTRACT

A guiding fixation method applied to an eye examination device includes a first light source and a second light source. The guiding fixation method includes disposing a third light source between the first light source and the second light source, when a distance between the eye examination device and an eye changes, the third light source emitting light to guide the eye to gaze at the third light source, and when the distance between the eye examination device and the eye stops changing, switching to the first light source and/or the second light source to emit light to guide the eye to gaze at the first light source and/or the second light source.

9 Claims, 4 Drawing Sheets

S10:
disposing at least one dummy light source between the first default light source and the second default light source S12:
when a distance between the eye examination device and an eye changes, the dummy light source emitting light to guide the eye to gaze at the dummy light source S14:
when the distance between the eye examination device and the eye stops changing, switching to the first default light source and/or the second default light source to emit light to guide the eye to gaze at the first default light source and/or the second default light source

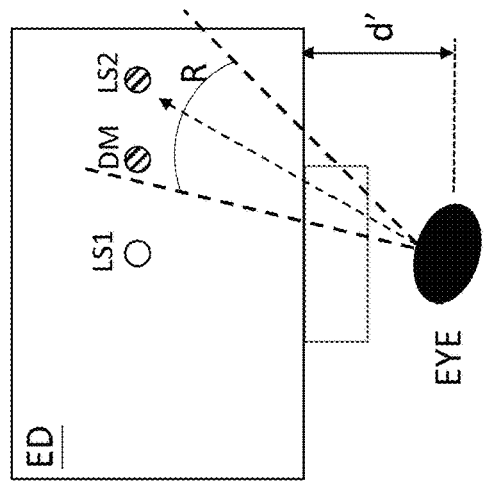
FIG. 2C
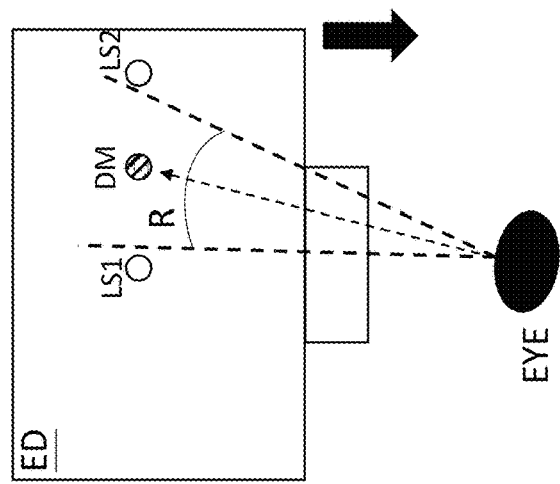
FIG. 2B
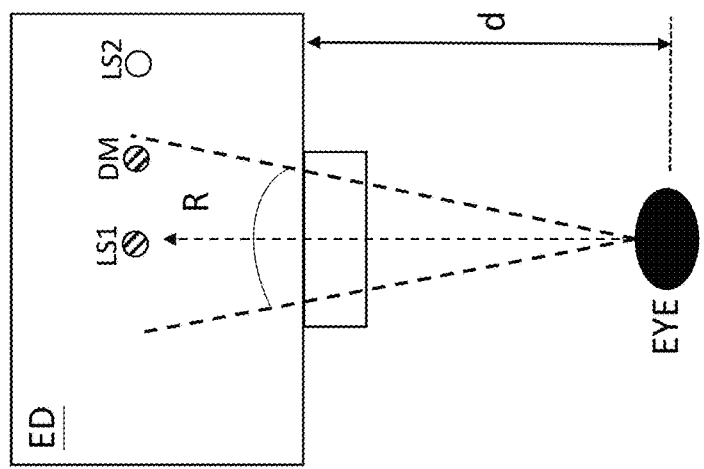
[FIG. 2A]

GUIDING FIXATION METHOD APPLIED TO EYE EXAMINATION DEVICE

CROSS-REFERENCE TO RELATED APPLICATIONS

This application claims the benefit of Taiwan patent application No. 110133091 filed on Sep. 6, 2021, and the entire content of which is hereby incorporated by reference herein in its entirety.

BACKGROUND OF THE INVENTION

Field of the Invention

The invention relates to an eye examination device; in particular, to a guiding fixation method applied to an eye examination device.

Description of the Prior Art

In general, the positions of default light sources (e.g., light-emitting diodes) disposed in the conventional eye examination devices are usually fixed (e.g., left and right sides). Under normal circumstances, the default light source of the eye examination device is within a visual range of the subject's eye, so as to provide lights to guide the subject's eye to perform detection. During the process of detecting the subject's eye by the eye examination device, the eye examination device sometimes needs to move to adjust the distance between the eye examination device and the subject's eye.

However, when the eye examination device moves toward the subject's eye, because the distance between the eye examination device and the subject's eye is shortened, the two default light sources of the eye examination device are likely to fall outside the visual range of the subject's eyes, so that the subject's eye needs to turn a considerable angle at a time, which needs to be improved.

SUMMARY OF THE INVENTION

Therefore, the invention provides a guiding fixation method applied to an eye examination device to solve the above-mentioned problems of the prior arts.

An embodiment of the invention is a guiding fixation method applied to an eye examination device. In this embodiment, the eye examination device at least includes a first default light source and a second default light source. The guiding fixation method includes steps of: (a) disposing at least one dummy light source between the first default light source and the second default light source; (b) when a distance between the eye examination device and an eye changes, the dummy light source emitting light to guide the eye to gaze at the dummy light source; and (c) when the distance between the eye examination device and the eye stops changing, switching to the first default light source and/or the second default light source to emit light to guide the eye to gaze at the first default light source and/or the second default light source.

In an embodiment, the change in the distance from the eye examination device to the eye in the step (b) means that the distance from the eye examination device to the eye is shortened.

In an embodiment, the distance from the eye examination device to the eye is shortened due to a movement of the eye examination device towards the eye.

In an embodiment, if an angle between a line of sight from the eye to the first default light source and a line of sight from the eye to the second default light source is an original rotation angle, a first rotation angle rotated by the eye changing from staring at the first default light source emitting light to staring at the dummy light source emitting light and a second rotation angle rotated by the eye from staring at the dummy light source emitting light to staring at the second default light source emitting light are both smaller than the original rotation angle, so that the eye does not need to rotate too much angle at a time.

In an embodiment, when the distance from the eye examination device to the eye has not changed, the first default light source is located within a visual range of the eye.

In an embodiment, the dummy light source is located within a visual range of the eye during the change in the distance from the eye examination device to the eye.

In an embodiment, when the distance from the eye examination device to the eye stops changing, the first default light source and/or the second default light source are located within a visual range of the eye.

In an embodiment, the first default light source, the second default light source and the dummy light source are arranged in line with each other.

In an embodiment, the first default light source, the second default light source and the dummy light source are arranged obliquely to each other.

In an embodiment, the dummy light source is a light-emitting diode (LED).

Compared to the prior art, during the period when the distance between the eye examination device and the subject's eye changes, the guiding fixation method of the invention will switch to the dummy light source disposed between the first default light source and the second default light source to provide lights to guide the subject's eye to gaze at it, which can effectively prevent the subject's eye from turning too large angle at a time, so as to improve the shortcomings of the prior art.

The advantage and spirit of the invention may be understood by the following detailed descriptions together with the appended drawings.

BRIEF DESCRIPTION OF THE APPENDED DRAWINGS

FIG. 2A illustrates a schematic diagram that the first default light source is disposed within the visual range of the eye when the distance from the eye examination device to the eye has not changed.

FIG. 2B illustrates a schematic diagram that the dummy light source is disposed within the visual range of the eye during the change of the distance from the eye examination device to the eye.

FIG. 2C illustrates a schematic diagram that the second default light source is disposed within the visual range of the eye when the distance from the eye examination device to the eye stops changing.

DETAILED DESCRIPTION OF THE INVENTION

Figure 1:
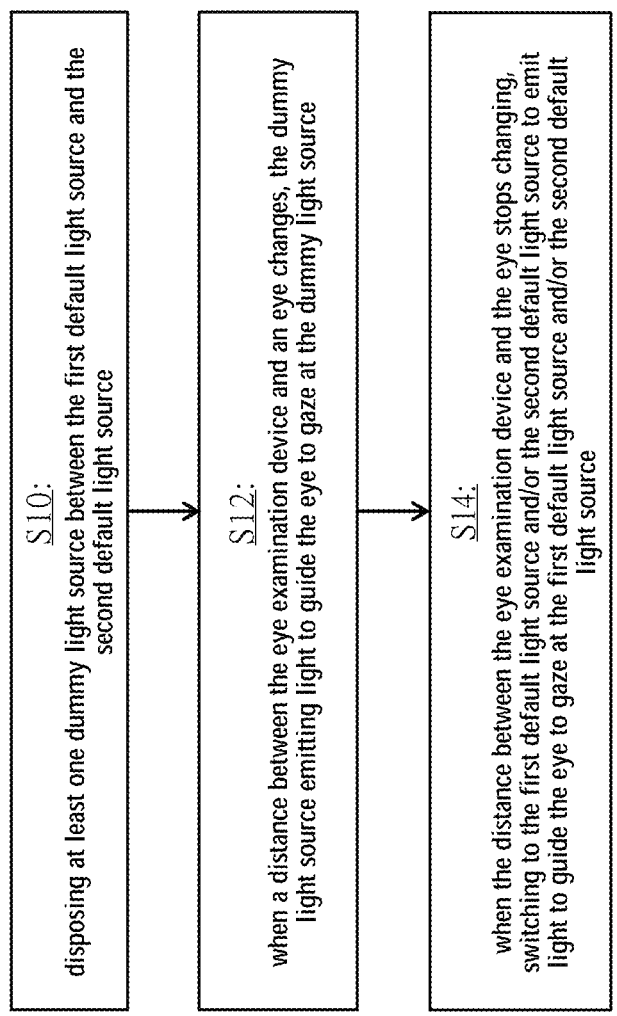
FIG. 1 illustrates a flowchart of the guiding fixation method in an embodiment of the invention.

Exemplary embodiments of the invention are referenced in detail now, and examples of the exemplary embodiments are illustrated in the drawings. Further, the same or similar reference numerals of the components/components in the drawings and the detailed description of the invention are used on behalf of the same or similar parts.

An embodiment of the invention is a guiding fixation method. In this embodiment, the guiding fixation method is applied to the period when the eye examination device detects the subject's eyes, but not limited to this. The eye examination device can provide one or more eye examination functions, and includes at least a first default light source and a second default light source.

Please refer to FIG. 1. FIG. 1 shows a flowchart of the guiding fixation method in this embodiment. As shown in FIG. 1, the guiding fixation method of this embodiment may include the following steps:

Step 10: disposing at least one dummy light source between the first default light source and the second default light source;

Step 12: when a distance between the eye examination device and an eye changes, the dummy light source emitting light to guide the eye to gaze at the dummy light source; and Step 14: when the distance between the eye examination device and the eye stops changing, switching to the first default light source and/or the second default light source to emit light to guide the eye to gaze at the first default light source and/or the second default light source.

In practical applications, the first default light source, the second default light source and the dummy light source can be light-emitting diodes (LEDs) or other types of light sources, and there is no specific limitation. The change in the distance between the eye examination device and the subject's eye in step S12 can be, for example, the movement of the eye examination device toward the subject's eye to shorten the distance between the eye examination device and the subject's eye, but not limited to this.

It should be noted that, since the dummy light source is disposed between the first default light source and the second default light source, it is assumed that an angle between the line of sight from the subject's eye to the first default light source and the line of sight from the subject's eye to the second default light source is an original rotation angle, and the subject's eye rotates a first rotation angle from gazing at the first default light source to gazing at the dummy light source and the subject's eye rotates a second rotation angle from gazing at the dummy light source to gazing at the second default light source, and the first rotation angle and the second rotation angle are both smaller than the original rotation angle, so that the subject's eye does not need to turn too much.

In an embodiment, the eye examination device ED can be provided with a distance detector to detect whether the distance between the eye examination device ED and the subject's eye changes, but not limited to this. When the distance detector detects that the distance between the eye examination device ED and the subject's eye changes, the eye examination device ED switches to the dummy light source disposed between the first default light source and the second default light source to emit lights to guide the subject's eye to look at the dummy light source. On the contrary, the eye examination device ED switches back to the first default light source and/or the second default light source to emit lights, so as to guide the subject's eye to gaze at the first default light source and/or the second default light source.

In an embodiment, when the distance between the eye examination device and the subject's eye has not changed, the first default light source is located within the visual range of the subject's eye. During the change in the distance between the eye examination device and the subject's eye, the dummy light source is located within the visual range of the subject's eye. When the distance between the eye examination device and the subject's eye stops changing, the first default light source and/or the second default light source are located within the visual range of the subject's eye.

For example, as shown in FIG. 2A, when the distance d from the eye examination device ED to the subject's eye EYE has not changed, the first default light source LS1 of the eye examination device ED is located within the visible range R of the subject's eye EYE, the first default light source LS1 of the eye examination device ED provides lights to guide the subject's eye EYE to gaze at the first default light source LS1.

As shown in FIG. 2B, when the eye examination device ED moves toward the subject's eye EYE, during the period when the distance between the eye examination device ED and the subject's eye EYE changes, the eye examination device ED is switched to the dummy light source DM disposed between the first default light source LS1 and the second default light source LS2 to emit lights to guide the subject's eye EYE to rotate to gaze at the dummy light source DM. At this time, the subject's eye EYE does not need to rotate too much angle. It should be noted that, during the period when the distance between the eye examination device ED and the subject's eye EYE changes, the first default light source LS1 and the second default light source LS2 can be located in the visual range R of the subject's eye EYE, but not limited to this.

As shown in FIG. 2C, when the eye examination device ED stops moving toward the subject's eye EYE, that is to say, when the distance from the eye examination device ED to the subject's eye EYE becomes d' and stops changing, the eye examination device ED is switched to the second default light source LS2 to emit lights to guide the subject's eye EYE to rotate to gaze at the second default light source LS2. At this time, the subject's eye EYE does not need to rotate too much angle at a time.

Figure 3B:
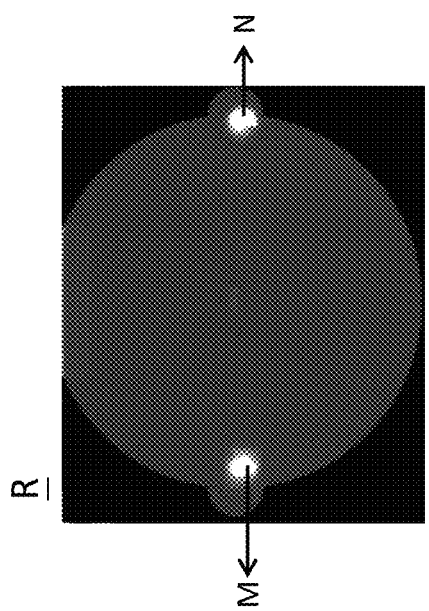
FIG. 3A and FIG. 3B illustrate schematic diagrams of determining whether the eye examination device and the subject's eye have reached an appropriate working distance according to two light spots.
Figure 3A:
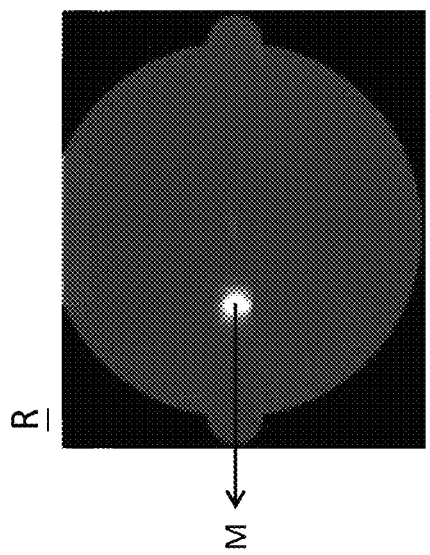

Please refer to FIG. 3A and FIG. 3B, the light spot M and the light spot N in FIG. 3A are used for detecting working distance, when the light spot M and the light spot N are located in symmetrical positions within the visible range R of the subject's eye EYE and focused, it means that the relative distance between the eye examination device ED and the subject's eye EYE in the three axes of X, Y, and Z has reached an appropriate working distance.

When the subject's eye EYE rotates, the light spot M and the light spot N will also move accordingly. Once the subject's eye EYE is rotated by a large angle as in the prior art, the light spot M and/or the light spot N is likely to move out of the visual range R of the eye EYE, as shown in FIG. 3B. Therefore, as shown in FIG. 2A to FIG. 2C, the subject's eye EYE does not need to rotate too much angle at a time due to the configuration of the dummy light source DM in the invention, so that the condition that the light spot M and/or the light spot N moves out of the visual range R of the eye EYE in the prior art can be effectively avoided.

Figure 4B:
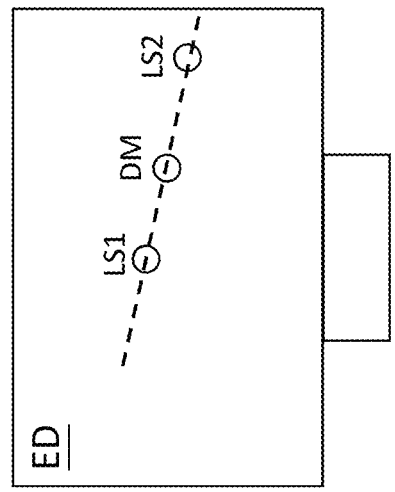
FIG. 4B illustrates a schematic diagram that the first default light source, the second default light source and the dummy light source are arranged obliquely to each other.
Figure 4A:
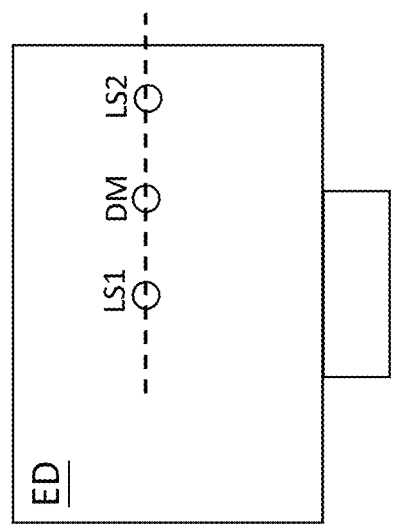
FIG. 4A illustrates a schematic diagram that the first default light source, the second default light source and the dummy light source are arranged in a straight line with each other.

In practical applications, the first default light source LS1, the second default light source LS2 and the dummy light source DM of the eye examination device ED can be arranged in different ways according to actual requirements. For example, as shown in FIG. 4A, the first default light source LS1, the second default light source LS2 and the dummy light source DM can be arranged in a straight line with each other; as shown in FIG. 4B, the first default light source LS1, the second default light source LS2 and the dummy light source DM can be arranged obliquely to each other.

Compared to the prior art, during the period when the distance between the eye examination device and the subject's eye changes, the guiding and fixing method of the invention will switch to the dummy light source disposed between the first default light source and the second default light source to provide lights to guide the subject's eye to gaze at it, which can effectively prevent the subject's eye from turning too large angle at a time, so as to improve the shortcomings of the prior art.

With the example and explanations above, the characteristics and spirits of the invention will be hopefully well described. Those skilled in the art will readily observe that numerous modifications and alterations of the device may be made while retaining the teaching of the invention. Accordingly, the above disclosure should be construed as limited only by the metes and bounds of the appended claims.

What is claimed is:

1. A guiding fixation method applied to an eye examination device, the eye examination device at least comprising a first light source and a second light source, the guiding fixation method comprising steps of:
    (a) disposing a third light source between the first light source and the second light source;
    (b) when a distance between the eye examination device and an eye changes, the third light source emitting light to guide the eye to gaze at the third light source; and
    (c) when the distance between the eye examination device and the eye stops changing, switching to the first light source and/or the second light source to emit light to guide the eye to gaze at the first light source and/or the second light source.

2. The guiding fixation method of claim 1, wherein the change in the distance from the eye examination device to the eye in the step (b) means that the distance from the eye examination device to the eye is shortened.

3. The guiding fixation method of claim 2, wherein the distance from the eye examination device to the eye is shortened due to a movement of the eye examination device towards the eye.

4. The guiding fixation method of claim 1, wherein if an angle between a line of sight from the eye to the first light source and a line of sight from the eye to the second light source is an original rotation angle, a first rotation angle rotated by the eye changing from staring at the first light source emitting light to staring at the third light source emitting light and a second rotation angle rotated by the eye from staring at the third light source emitting light to staring at the second light source emitting light are both smaller than the original rotation angle, so that the eye does not need to rotate too much angle at a time.

5. The guiding fixation method of claim 1, wherein when the distance from the eye examination device to the eye has not changed, the first light source is located within a visual range of the eye.

6. The guiding fixation method of claim 1, wherein the third light source is located within a visual range of the eye during the change in the distance from the eye examination device to the eye.

7. The guiding fixation method of claim 1, wherein when the distance from the eye examination device to the eye stops changing, the first light source and/or the second light source are located within a visual range of the eye.

8. The guiding fixation method of claim 1, wherein the first light source, the second light source and the third light source are arranged in line with each other.

9. The guiding fixation method of claim 1, wherein the third light source is a light-emitting diode (LED).

* * * * *